(12) United States Patent
Urschel et al.

(10) Patent No.: US 11,448,630 B2
(45) Date of Patent: Sep. 20, 2022

(54) PLANT FLUOROMETER FOR REMOTE DETECTION OF GROWTH DYNAMICS

(71) Applicant: RENSSELAER POLYTECHNIC INSTITUTE, Troy, NY (US)

(72) Inventors: Matthew R. Urschel, Troy, NY (US); Andrew Turk, Troy, NY (US); Tessa Hilary Pocock, Troy, NY (US)

(*) Notice: Subject to any disclaimer, the term of this patent is extended or adjusted under 35 U.S.C. 154(b) by 271 days.

(21) Appl. No.: 16/786,278

(22) Filed: Feb. 10, 2020

(65) Prior Publication Data

US 2020/0256841 A1 Aug. 13, 2020

Related U.S. Application Data

(60) Provisional application No. 62/802,886, filed on Feb. 8, 2019.

(51) Int. Cl.
*G01N 33/00* (2006.01)
*G01N 21/64* (2006.01)

(52) U.S. Cl.
CPC ......... *G01N 33/0098* (2013.01); *G01N 21/64* (2013.01); *G01N 2201/062* (2013.01); *G01N 2201/0696* (2013.01)

(58) Field of Classification Search
CPC .............. G01N 33/0098; G01N 21/64; G01N 2201/062; G01N 2201/0696
See application file for complete search history.

(56) References Cited

U.S. PATENT DOCUMENTS

| 4,084,905 | A | 4/1978 | Schreiber et al. |
| 8,850,742 | B2 | 10/2014 | Dube |
| 2019/0059202 | A1* | 2/2019 | Lorek .................. A01G 25/167 |

FOREIGN PATENT DOCUMENTS

| DE | 3518527 A1 | 7/1987 |
| EP | 3045033 A1 | 7/2016 |

OTHER PUBLICATIONS

Bankestad, D., et al., "Growth tracking of basil by proximal remote sensing of chlorophyll fluorescence in growth chamber and greenhouse environments," Computers and Electronics in Agriculture, vol. 128, pp. 77-86, 2016.

* cited by examiner

*Primary Examiner* — Georgia Y Epps
*Assistant Examiner* — Don J Williams
(74) *Attorney, Agent, or Firm* — Murtha Cullina LLP; Anthony P. Gangemi

(57) ABSTRACT

An apparatus for remote detection of plant growth dynamics is described. The apparatus includes an excitation LED (light emitting diode) module, a detection module and a controller module coupled to the excitation LED module and the detection module. The excitation LED module includes at least one LED. Each LED is configured to emit an excitation light in response to an excitation control signal. The excitation light has an emitted light spectrum.

The detection module includes a photodetector configured to detect an initial chlorophyll a fluorescence ("ChlF") light and an excited ChlF light from a plant species. The photodetector is further configured to convert the detected initial ChlF light into an initial detection electrical signal and the detected excited ChlF light into an excited detection electrical signal. The excited ChlF light is emitted from the plant species in response to receiving the excitation light.

The controller module is configured to provide the excitation control signal to the excitation module, to capture the initial and excited detection electrical signals from the detection module and to determine chlorophyll fluorescence data based, at least in part, on the initial and excited detection electrical signals. The excitation LED module and the detection module are configured to be positioned remotely from (Continued)

the plant species. The chlorophyll fluorescence data represents a growth characteristic of the plant species.

18 Claims, 3 Drawing Sheets

PLANT FLUOROMETER FOR REMOTE DETECTION OF GROWTH DYNAMICS

CROSS REFERENCE TO RELATED APPLICATION(S)

This application claims the benefit of U.S. Provisional Application No. 62/802,886, filed Feb. 8, 2019, which is incorporated by reference as if disclosed herein in its entirety.

GOVERNMENT LICENSE RIGHTS

This invention was made with government support under grant no. EEC0812056, awarded by the National Science Foundation. The government has certain rights in the invention.

FIELD

The present disclosure is related to a plant fluorometer, in particular to, a plant fluorometer for remote detection of growth dynamics.

BACKGROUND

Evidence for anthropogenic climate change along with predicted demographic trends toward increased habitation in cities are imposing new challenges on global agriculture and are threatening food security for a global population that is projected to reach 11.2 billion people by the end of the 21st century. This, together with the growing demand for fresh, locally-grown produce and shifts toward plant-based diets has attracted renewed interest in controlled environment agriculture (CEA).

The production of food crops in CEA can help mitigate food insecurity, protects crops from inclement weather, and allows for consistent and predictable crop production through rigorous environmental control. CEA sensing and control systems have existed for over fifty years and typically involve the control of environmental parameters, such as light, temperature, $CO_2$, and relative humidity. Real-time environmental data are used to modulate ventilation, heating, fog systems, shade systems, and supplemental lighting.

Lighting is a design component for crop growth via CEA, and is undergoing rapid advances with the advent of tunable, light emitting diode (LED) systems. Electric lighting can account for up to 30% of the total energy cost, but is optimized to make CEA more economically viable while also reducing its carbon footprint. The daily light integral is the accumulated light reaching the canopy, and is measured as moles of photons $m^{-2}$ $day^{-1}$ within the photosynthetically-active radiation (PAR) region of 400-700 nm. It is specific for different crops and is positively correlated with growth and crop yield. Most light control systems are based on instantaneous light values, past weather, or predictive weather patterns, but systems based on the accumulation of PAR during the day (DLI) have resulted in further optimization of crop yield and energy use. Use of supplemental and sole source (no sun) lighting technology is expanding in CEA as the importance of spectral variation on plant growth and physiological responses becomes apparent.

The integration of these systems into existing CEA environmental control architectures is in its infancy and would benefit from a non-invasive, rapid, real-time, remote sensor that could track crop growth under different lighting regimes. Additionally, new methods and models are desired to quantify crop growth remotely and non-invasively, better predict crop growth using different lighting technologies, assess the performance of new cultivars, and advance the state of the art in CEA through knowledge gained from fundamental research.

SUMMARY

In an embodiment, there is provided an apparatus for remote detection of plant growth dynamics. The apparatus includes an excitation LED (light emitting diode) module, a detection module and a controller module coupled to the excitation LED module and the detection module. The excitation LED module includes at least one LED. Each LED is configured to emit an excitation light in response to an excitation control signal. The excitation light has an emitted light spectrum.

The detection module includes a photodetector configured to detect an initial chlorophyll a fluorescence ("ChlF") light and an excited ChlF light from a plant species. The photodetector is further configured to convert the detected initial ChlF light into an initial detection electrical signal and the detected excited ChlF light into an excited detection electrical signal. The excited ChlF light is emitted from the plant species in response to receiving the excitation light.

The controller module is configured to provide the excitation control signal to the excitation module, to capture the initial and excited detection electrical signals from the detection module and to determine chlorophyll fluorescence data based, at least in part, on the initial and excited detection electrical signals. The excitation LED module and the detection module are configured to be positioned remotely from the plant species. The chlorophyll fluorescence data represents a growth characteristic of the plant species.

In some embodiments, the controller module is further configured to transmit the chlorophyll fluorescence data to a cloud service. In some embodiments, the excitation light has a wavelength of about 447 nanometers (nm) and each ChlF light has a wavelength selected from the group including about 680 nm and about 740 nm.

In some embodiments, the growth characteristic is selected from the group including relative growth rates (RGR), net assimilation rates (NAR), plant area (PA), leaf area ratio (LAR), or combinations thereof. In some embodiments, a relationship between a selected growth characteristic and the chlorophyll fluorescence data corresponds to a polynomial regression.

In some embodiments, the photodetector is selected from the group including a photodiode and a phototransistor. The detection module further includes a collimator coupled to the photodetector. The controller module includes a processing unit, a preprocessing amplifier, a lock in amplifier and a gain and filter stage. The processing unit is selected from the group including a single core processing unit, a microcontroller, an application-specific integrated circuit (ASIC), a field programmable gate array (FPGA) and a programmable logic device (PLD). The lock in amplifier is configured to pass a portion of each of the detection electrical signals. The portion has a fundamental frequency corresponding to a fundamental frequency of the excitation control signal.

In some embodiments, the excitation control signal includes an excitation pulse. The excitation pulse includes a pulse train defined by a plurality of excitation pulse parameters including a maximum current amplitude, a duty cycle, an excitation pulse period ($T_E$), a pulse train pulse period ($T_P$) and an excitation pulse fundamental frequency. A respective value of each of the plurality of the excitation pulse parameters is related to a growth dynamic of the plant species. The controller module is configured to capture the initial detection electrical signal prior to capturing the excited detection electrical signal.

In some embodiments, the maximum current amplitude corresponds to a photon flux density at a canopy of the plant species of 2000 micromoles of light per square meter per second ($\mu mol\ m^{-2}s^{-1}$) photosynthetically-active radiation (PAR), the duty cycle is 50 percent, the excitation pulse period (TE) is in the range of 0.5 seconds to 1 second, and the excitation pulse fundamental frequency is 200 hertz (Hz) corresponding to the pulse train pulse period ($T_P$) of 5 milliseconds.

In an embodiment, there is provided a method for remote detection of plant growth dynamics. The method includes providing, by a controller module, an excitation control signal to an excitation LED (light emitting diode) module; and emitting, by at least one LED included in the excitation LED module, an excitation light in response to the excitation control signal. The excitation light has an emitted light spectrum. The method further includes detecting, by a photodetector included in a detection module, an initial chlorophyll a fluorescence ("ChlF") light and an excited ChlF light from a plant species. The method further includes converting, by the photodetector, the detected initial ChlF light into an initial detection electrical signal and the detected excited ChlF light into an excited detection electrical signal. The excited ChlF light is emitted from the plant species in response to receiving the excitation light. The method further includes capturing, by the controller module, the initial and excited detection electrical signals from the detection module; and determining, by the controller module, chlorophyll fluorescence data based, at least in part, on the initial and excited detection electrical signals. The excitation LED module and the detection module are configured to be positioned remotely from the plant species. The chlorophyll fluorescence data represents a growth characteristic of the plant species.

In some embodiments, the method further includes transmitting, by the controller module, the chlorophyll fluorescence data to a cloud service. In some embodiments of the method, the excitation light has a wavelength of about 447 nanometers (nm) and each ChlF light has a wavelength selected from the group including about 680 nm and about 740 nm.

In some embodiments of the method, the growth characteristic is selected from the group including relative growth rates (RGR), net assimilation rates (NAR), plant area (PA), leaf area ratio (LAR), or combinations thereof. In some embodiments of the method, a relationship between a selected growth characteristic and the chlorophyll fluorescence data corresponds to a polynomial regression.

In some embodiments of the method, the photodetector is selected from the group including a photodiode and a phototransistor. The detection module further includes a collimator coupled to the photodetector. The controller module includes a processing unit, a preprocessing amplifier, a lock in amplifier and a gain and filter stage. The processing unit is selected from the group including a single core processing unit, a microcontroller, an application-specific integrated circuit (ASIC), a field programmable gate array (FPGA) and a programmable logic device (PLD). The lock in amplifier is configured to pass a portion of each of the detection electrical signals, the portion having a fundamental frequency corresponding to a fundamental frequency of the excitation control signal.

In some embodiments, the method further includes capturing, by the controller module, the initial detection electrical signal prior to capturing the excited detection electrical signal. The excitation control signal includes an excitation pulse. The excitation pulse includes a pulse train defined by a plurality of excitation pulse parameters including a maximum current amplitude, a duty cycle, an excitation pulse period ($T_E$), a pulse train pulse period ($T_P$) and an excitation pulse fundamental frequency. A respective value of each the plurality of the excitation pulse parameters is related to a growth dynamic of the plant species.

In some embodiments of the method, the maximum current amplitude corresponds to a photon flux density at a canopy of the plant species of 2000 micromoles of light per square meter per second ($\mu mol\ m^{-2}s^{-1}$) photosynthetically-active radiation (PAR), the duty cycle is 50 percent, the excitation pulse period ($T_E$) is in the range of 0.5 seconds to 1 second, and the excitation pulse fundamental frequency is 200 hertz (Hz) corresponding to the pulse train pulse period ($T_P$) of 5 milliseconds.

In an embodiment, there is provided a system for remote detection of plant growth dynamics. The system includes sensing circuitry and a cloud service coupled to the sensing circuitry via a network. The sensing circuitry includes an excitation LED (light emitting diode) module, a detection module and a controller module coupled to the excitation LED module and the detection module. The excitation LED module includes at least one LEI). Each LEI) is configured to emit an excitation light in response to an excitation control signal. The excitation light has an emitted light spectrum.

The detection module includes a photodetector configured to detect an initial chlorophyll a fluorescence ("ChlF") light and an excited ChlF light from a plant species. The photodetector is further configured to convert the detected initial ChlF light into an initial detection electrical signal and the detected excited ChlF light into an excited detection electrical signal. The excited Chlf light is emitted from the plant species in response to receiving the excitation light.

The controller module is configured to provide the excitation control signal to the excitation module, to capture the initial and excited detection electrical signals from the detection module and to determine chlorophyll fluorescence data based, at least in part, on the initial and excited detection electrical signals. The excitation LED module and the detection module are configured to be positioned remotely from the plant species. The chlorophyll fluorescence data represents a growth characteristic of the plant species. The excitation LED module and the detection module are configured to be positioned remotely from the plant species. The chlorophyll fluorescence data represents a growth characteristic of the plant species.

The cloud service includes a data store. The controller module is configured to transmit the chlorophyll fluorescence data to the cloud service for storage in the data store.

In some embodiments of the system, the growth characteristic is selected from the group including relative growth rates (RGR), net assimilation rates (NAR), plant area (PA), leaf area ratio (LAR), or combinations thereof. In some embodiments of the system, the cloud service further includes a cloud analysis application configured to determine a relationship between a selected growth characteristic and the chlorophyll fluorescence data. In some embodiments of the system, the relationship between the selected growth characteristic and the chlorophyll fluorescence data corresponds to a polynomial regression.

BRIEF DESCRIPTION OF THE DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein.

DETAILED DESCRIPTION

Figure 1:
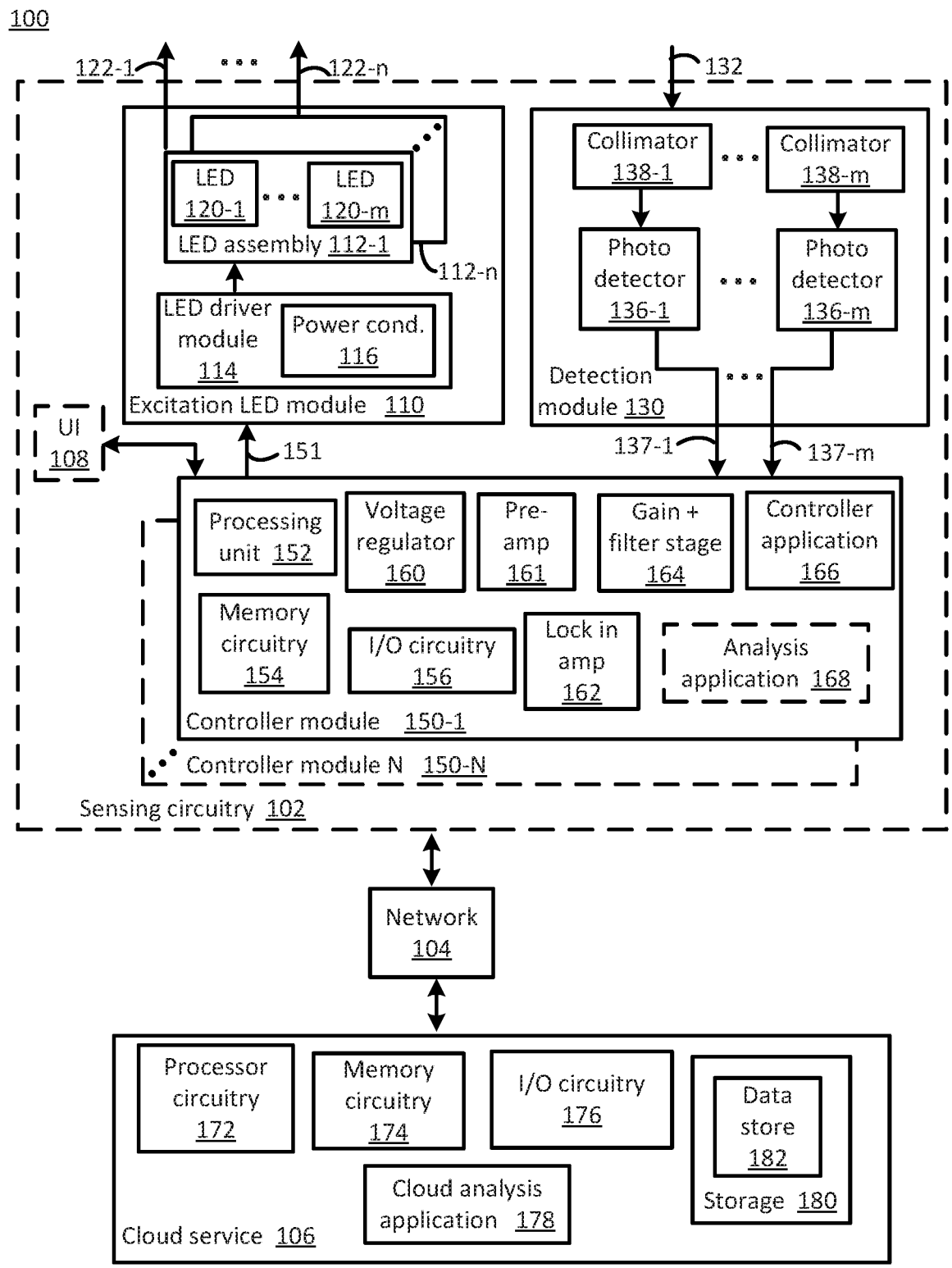
FIG. 1 illustrates a functional block diagram of a plant fluorometer system for remote detection of growth dynamics consistent with several embodiments of the present disclosure.

Generally, calculating RGR from direct physical measurements of plant mean fresh weight (FW) or mean dry weight (DW) can be laborious and is destructive to plants. A simple and non-destructive method for collecting time series growth data remotely may facilitate studies of growth kinetics. A number of techniques for remotely sensing plant growth have been investigated over the last several decades. Development of plant growth models based on image processing, machine vision and neural networks for photographic growth monitoring have been in use since the 1990s, but these methods have not been widely adopted. Image sensing and processing have been used to predict crop harvest dates for lettuce and time to first flower for tomatoes, however, this method involves heavy computation and is sensitive to ambient light or changes in other environmental parameters. Although typically used in satellite imaging, several different ChlF platforms have been described that can be used to measure growth or photosynthetic performance in CEA settings.

Chlorophyll fluorescence is a natural process whereby light energy absorbed by chlorophyll a molecules is re-emitted as light in the red and far-red regions. The chlorophyll a fluorescence (ChlF) emission spectrum at room temperature ranges from approximately 650 nm to 780 nm with relatively distinct peak maxima at 685 nm and between 720-740 nm. The measurement of ChlF is non-invasive and relatively fast and has been used as a probe for photosynthetic activity, to detect stress and to understand photosynthetic regulation of biochemical pathways and gene expression. Functionally, ChlF yields are inversely proportional to photosynthetic rates.

ChlF may be a useful tool to test agricultural productivity, physiological status of newly bred cultivars, the health of fresh produce, and in optimizing plant growth conditions (i.e., temperature, light, etc.) for economic optimization of crop plants in CEA. There are a number of ChlF methodologies based on different instruments and timescales of data capture, but they use direct contact or relatively close proximity to the leaf (i.e., <2.0 cm). Some ChlF fluorometers include two components. The first involves active (lamps, lasers) or passive (solar) light-induced excitation of chlorophyll a molecules. The second component measures the resulting ChlF using optical fibers, satellite images, or photodiodes. Spectroradiometers employing optical fiber systems have been used for direct ChlF measurements and these measurements have been shown to correlate with growth and photosynthetic efficiency. A relationship has also been observed between dry weight accumulation and spectrally sensed red (665-675 nm) to far-red (740-750 nm) ratios in basil crops. Most commercial pulse amplitude modulated ChlF research systems used in stress physiology and ecophysiology use photodiodes as sensors. Photodiodes are relatively low cos, relatively small, and have a relatively fast response time. Thus, it is contemplated that ChlF may be a good candidate for the advancement of crop growth modeling.

Kinetic growth analyses provide insight into the rates of plant physiological processes underlying growth and allow plant growth outcomes to be predicted and adjusted. Additionally or alternatively kinetic growth may be a useful research tool for assessing the effects of different environments on plants or the performance of newly bred cultivars.

In some embodiments of the present disclosure, a fluorescence sensing device is described that provides direct, remote, real-time physiological data collection for integration into tunable LED lighting control systems, thereby enabling energy efficiency and better control of crop growth. Data collected by this device can be used to model growth of target plants, e.g., red lettuce. Additionally or alternatively to monitoring growth, it is contemplated that a system consistent with the present disclosure may be used to predict relative growth rates (RGR), net assimilation rates (NAR), plant area (PA), and leaf area ratio (LAR).

FIG. 1 illustrates a functional block diagram 100 of a plant fluorometer system for remote detection of growth dynamics, consistent with several embodiments of the present disclosure. In some embodiments, plant fluorometer system 100 may be configured to remotely detect a fluorescent species in order to monitor growth of a plant species in real-time. In some embodiments, the fluorescent species includes chlorophyll a fluorescence (ChlF). In one nonlimiting example, the system 100 may be used to monitor real-time growth dynamics, e.g., of Red Oakleaf lettuce (Lactuca sativa cv. Rouxai) grown in controlled environment growth chambers. However, this disclosure is not limited in this regard. In another nonlimiting example, regression analysis may then be used to construct models from captured data that relates observed growth dynamics to measured ChlF (chlorophyll a fluorescence) data.

System 100 includes sensing circuitry 102, a network 104 and a cloud service 106. In an embodiment, sensing circuitry 102 may be positioned relative to a plant species being evaluated. Sensing circuitry 102 may be coupled, wired and/or wirelessly to network 104 and may be further coupled to cloud service 106 by network 104.

Sensing circuitry 102 includes excitation light emitting diode (LED) module 110, detection module 130 and one or more controller modules 150-1, . . . , 150-N. In some embodiments, sensing circuitry 102 may further include user interface (UI) 108. In an embodiment, each controller module, e.g., controller module 150-1, is coupled to the excitation LED module 110 and the detection module 130.

Excitation LED module 110 includes one or more LED assemblies 112-1, . . . , 112-n, and an LED driver module 114. The LED driver module 114 may include power conditioning 116. Power conditioning 116 may include, for example, resistors and/or voltage regulators to condition the power to the LED assemblies. Each LED assembly, e.g., LED assembly 112-1, may include a plurality of LEDs 120-1, ..., 120-m. In one nonlimiting example, the excitation LED module 110 may include four LED assemblies. However, this disclosure is not limited in this regard. In one nonlimiting example, the LED assembly 112-1 may include three LEDs. However, this disclosure is not limited in this regard. Excitation LED module 110 may be enclosed in an enclosure configured to protect the elements of the excitation LEI) module from the environment.

Detection module 130 includes one or more photo detectors 136-1, ..., 136-m. Photo detectors may include, but are not limited to, photodiodes, photo transistors, etc. It may be appreciated that photodiodes and/or photo transistors may be relatively less expensive, may occupy relatively less space and may consume relatively less power compared to, for example, a photomultiplier tube. Detection module 130 may further include one or more collimators 138-1, ..., 138-m. Generally, each collimator, e.g., collimator 138-1, may be associated with a respective photodetector, i.e., collimator 138-1 may be associated with photodetector 136-1. The collimators, e.g., collimator 138-1, are configured to limit incoming light to a selected wavelength and/or field of view. In one nonlimiting example, collimator 138-1 may correspond to a near collimated optical filter. However, this disclosure is not limited in this regard.

Each controller module, e.g., controller module 150-1 may include a processing unit 152, memory circuitry 154 and input/output (I/O) circuitry 156. Each controller module may further include a voltage regulator 160, a pre amplifier 161, a lock in amplifier 162 and a gain and filter stage 164. Each controller module 150-1 may further include a controller application 166. In some embodiments, controller module 150-1 may further include an analysis application 168.

Processing unit 152 may include, but is not limited to, a single core processing unit, a microcontroller, an application-specific integrated circuit (ASIC), a field programmable gate array (FPGA), a programmable logic device (PLD), etc. Processing unit 152 may be configured to perform one or more operations of controller module 150-1. Memory circuitry 154 may include one or more types of memory, as described herein. Memory circuitry 154 may be configured to store information and/or data associated with processing unit 152, controller application 166 and/or analysis application 168.

User interface 108 may include a user input device (e.g., keyboard, keypad, mouse, touchpad, touch sensitive display, a microphone, one or more joysticks, etc.) and a user output device (e.g., a display, a loudspeaker, a visual indicator (e.g., light bulb, light emitting diode (LED), etc.).

Cloud service 106 includes processor circuitry 172, memory circuitry 174, I/O circuitry 176, and storage 180. Cloud service 106 may further include a cloud analysis application 178. Storage 180 may include data store 182. In an embodiment, data store 182 may be configured to store chlorophyll fluorescence data, as described herein.

Figure 2:
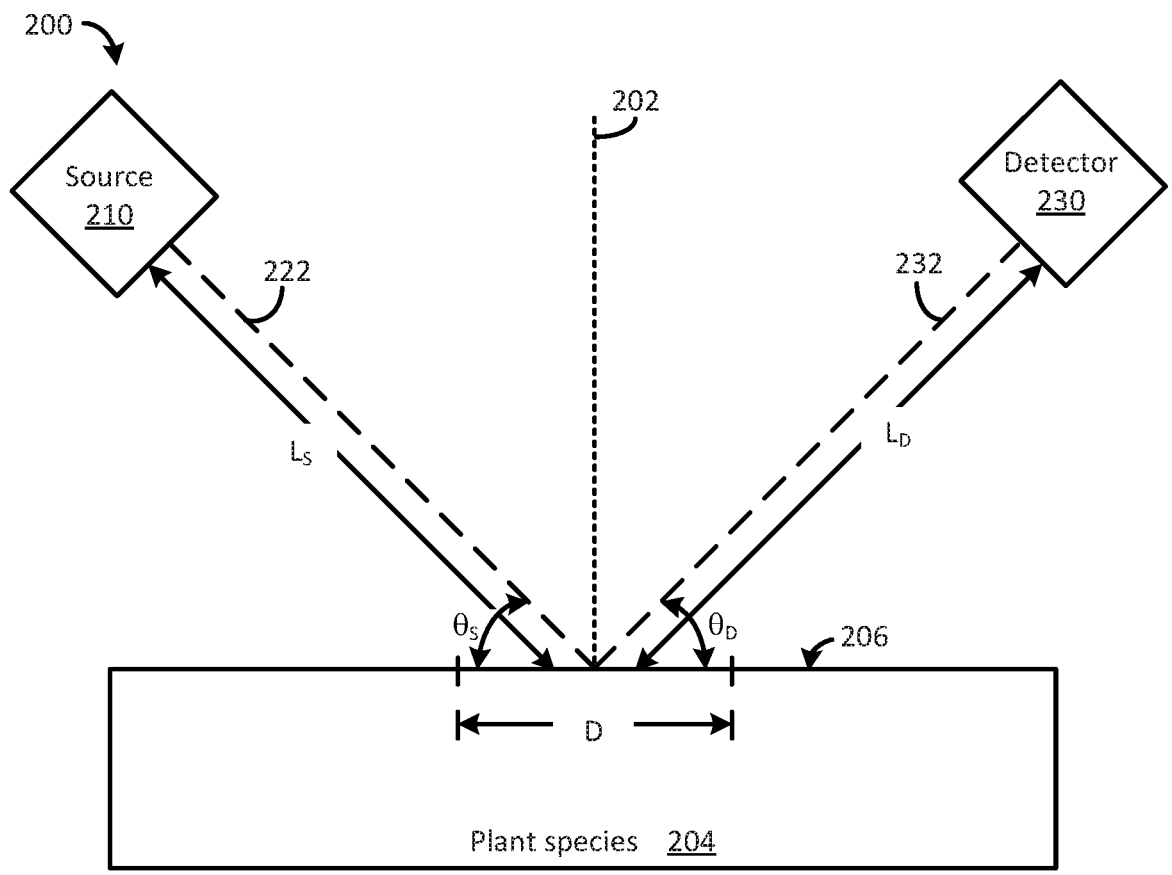
FIG. 2 is a sketch illustrating one example of relative locations of a plant species, a source and detector, consistent with one example of the present disclosure.

FIG. 2 is a sketch 200 illustrating relative locations of a plant species 204, a source 210 and a detector 230, consistent with several embodiments of the present disclosure. The plant species 204 has a corresponding crop canopy 206. Sketch 200 includes a centerline 202 positioned generally perpendicular to the crop canopy 206. Sketch 200 further includes a source module ("source") 210 and a detector module ("detector") 230. In one nonlimiting example, excitation LED module 110 of FIG. 1 may correspond to source 210 and detection module 130 may correspond to detector 230.

The source 210 and detector 230 are positioned relative to crop species 204 and crop canopy 206. In some embodiments, the source 210 and a detector 230 may be positioned remote from the plant species 204 being monitored. In an embodiment, source 210 may be positioned a distance, $L_S$, and at an angle $\theta_S$, relative to the crop canopy 206. Similarly, detector 230 may be positioned a distance, $L_D$, and at an angle $\theta_D$ from the crop canopy 206. In an embodiment the angles may be equal. In some embodiments, $L_S$ and $L_D$ may be between about 30 cm (centimeters) to about 100 cm. In some embodiments, $L_S$ and $L_D$ may be about 50 cm. Thus, in these embodiments, the source 210 and the detector 230 may be positioned about 50 cm from the plant canopy 206 and plant species 204. In some embodiments, the angles $\theta_S$ and $\theta_D$, may be between about 30 degrees to about 60 degrees. In some embodiments, the excitation light source and the photodiode components are placed at an angle ($\theta_S$ and $\theta_D$) to the plant species of about 45 degrees. Thus, the excitation LED module and the detection module are configured to be positioned remotely from the plant species. Source 210 is configured to emit light at a frequency or frequencies and line 222 may correspond to a centerline of the emitted light. Detector 230 is configured to detect fluorescence emitted by plant species 204 in response to received emitted light from source 210. Detector 230 may be positioned with a field of view corresponding to a diameter, D. In some embodiments, the field of view of the photodiodes, and thus the area of the crop being sensed, is about 10 cm to about 20 cm in diameter. In some embodiments, the field of view of the photodiodes is about 12 cm in diameter.

Turning again to FIG. 1, excitation LED module 110 may be configured to emit light 122-1, ..., 122-n. The emitted light may have a corresponding emitted light spectrum. In an embodiment, the corresponding emitted light spectrum may correspond to a range of blue, e.g., wavelengths in a range of 450 nanometers (nm)±15 nm. In an embodiment, each LED assembly 112-1, ..., 112-m may be configured to emit an excitation light. For example, each LEI) 120-1, ..., 120-m may be configured to emit the excitation light. The excitation light may be emitted in response to an excitation control signal from, for example, controller module 150-1. In one nonlimiting example, the excitation light may have a wavelength of about 447 nm. In one nonlimiting example, the emitted light may result in a photon flux density at a canopy of the plant species of 2000 micromoles of light per square meter per second ($\mu mol\ m^{-2}s^{-1}$) photosynthetically-active radiation (PAR).

Detection module 130 may be configured to detect light 132. The detected light may have a corresponding spectrum. In one nonlimiting example, the detected light may have a wavelength at or near 680 nm. In another example, the detected light might have a wavelength at or near 740 nm. In an embodiment, each photodetector, e.g., photodetector 136-1, may be configured to detect light. In an example, the detected light may include an initial chlorophyll a fluorescence (ChlF) light from a plant species, e.g., plant species 204. In another example, the detected light may include an excited ChlF light from the plant species 204. The photodetector 136-1 may be configured to convert the detected initial ChlF light into an initial detection electrical signal and the detected excited ChlF light into an excited detection electrical signal. The excited ChlF light may be emitted from the plant species 204 in response to receiving the excitation light. Each ChlF light may then have a wavelength selected from the group including about 680 nm and about 740 nm.

The controller modules, e.g., controller module 150-1, are configured to provide an excitation control signal 151 to excitation LED module 110. Controller module 150-1 is further configured to capture one or more detection signals 137-1, ..., 137-$m$ from detection module 130. The detection signals may be related to the detected light 132. In an example, the detection signals may include an initial detection electrical signal related to the initial ChlF light. In another example, the detection signals may include an excited detection electrical signal related to the excited ChlF light. The controller module 150-1 is further configured to determine chlorophyll fluorescence data based, at least in part, on the initial and excited detection electrical signals. In an embodiment, the chlorophyll fluorescence data represents a growth characteristic of the plant species. The growth characteristic may include, but is not limited to, relative growth rates (RGR), net assimilation rates (NAR), plant area (PA), leaf area ratio (LAR), and/or combinations thereof. In some embodiments, the controller module 150-1 may be further configured to transmit the chlorophyll fluorescence data to the cloud service 106.

The growth characteristics include physiological changes that may be related to environmental stressors, e.g., drought, nutrient limitation, temperature, disease, etc., or combinations thereof. The relative growth rate (RGR) of a plant is defined as the rate of mass increase per unit mass present, and provides a measure of the efficiency of plant growth normalized to total biomass. Evaluating the RGR is configured to allow for an equitable comparison of growth rates between different plant species or individuals by accounting for variations in scale between them. The RGR may be predictive of plant mortality and can indicate the nutritional status of plants. Plant growth kinetic analyses can be fitted to a linear or exponential model and the RGR may then be calculated as a slope of the natural logarithm-transformed mean fresh (FW) or dry (DW) weight.

Figure 3:
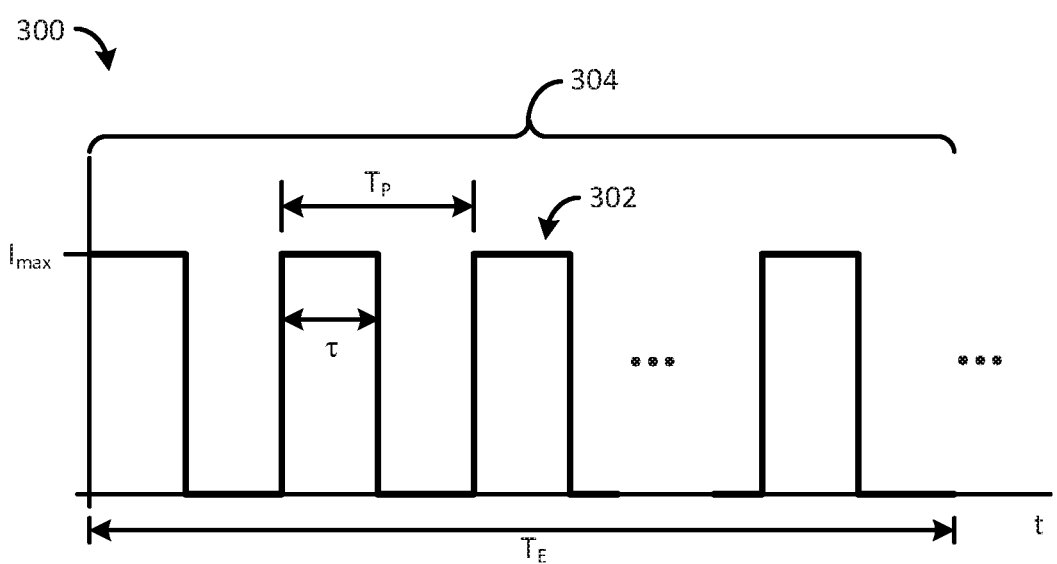
FIG. 3 is a plot of one example excitation control signal, consistent with one embodiment of the present disclosure.

FIG. 3 is a plot 300 of one example excitation control signal 302 consistent with one embodiment of the present disclosure. The excitation control signal 302 includes an excitation pulse 304 having an excitation pulse period ($T_E$). The excitation pulse 304 includes a pulse train defined by a plurality of excitation pulse parameters. The excitation pulse parameters include, but are not limited to, a maximum current amplitude ($I_{max}$), a pulse train pulse period ($T_P$), a duty cycle ($\tau/T_P$) and an excitation pulse fundamental frequency ($1/T_P$). A respective value of each of the plurality of the excitation pulse parameters may be related to a growth dynamic of the plant species. In one nonlimiting example, the maximum current amplitude, $I_{max}$, corresponds to a photon flux density at a canopy of the plant species of 2000 micromoles of light per square meter per second ($\mu$mol m$^{-2}$s$^{-1}$) photosynthetically-active radiation (PAR), the duty cycle is 50 percent, the excitation pulse period ($T_E$) is in the range of 0.5 seconds to 1 second, and the excitation pulse fundamental frequency is 200 hertz (Hz) corresponding to the pulse train pulse period ($T_P$) of 5 milliseconds. In some embodiments, the ChlF measurements may be configured to occur at a time interval (i.e., excitation pulse duration, $T_E$) greater than about 0.5 second (s). In some embodiments, the ChlF measurements may be configured to occur at a time interval ($T_E$) greater than about 0.8 s. In some embodiments, the ChlF measurements occur at a time interval ($T_E$) greater than about 1 s. In some embodiments, measurements may be configured to occur every 1, 5, 10, 15, 20, 30, 60, or more minutes. In other words, an excitation pulse of duration $T_E$ may be configured to occur at a repetition interval, $T_R$, and $T_R$ may be selected from the group including 1, 5, 10, 15, 20, 30, 60, or more minutes.

Turning again to FIG. 1, the voltage regulator 160 is configured to receive a power supply voltage, e.g. 12 volts, and to provide regulated voltage(s), e.g., ±5 V, to power, for example, other elements of controller module 150-1 and detection module 130. Controller application 166 may be configured to manage capture and at least some processing of the initial and excited detection electrical signals received from detection module 130. For example, the excited detection electrical signal may be initially processed by pre amplifier 161 then lock in amplifier 162 and then gain and filter stage 164. The lock in amplifier 162 may be configured to receive a reference signal with a reference frequency corresponding to the excitation pulse fundamental frequency. The lock in amplifier 162 may then be configured to pass excited detection electrical signal intensity at the excitation pulse fundamental frequency and to reject excited detection electrical signal intensity at other than the excitation pulse fundamental frequency. Gain and filter stage 164 may then be configured to amplify and low pass filter the output signal from the lock in amplifier 162. Corresponding chlorophyll fluorescence data may then be determined, as described herein.

Figure 4:
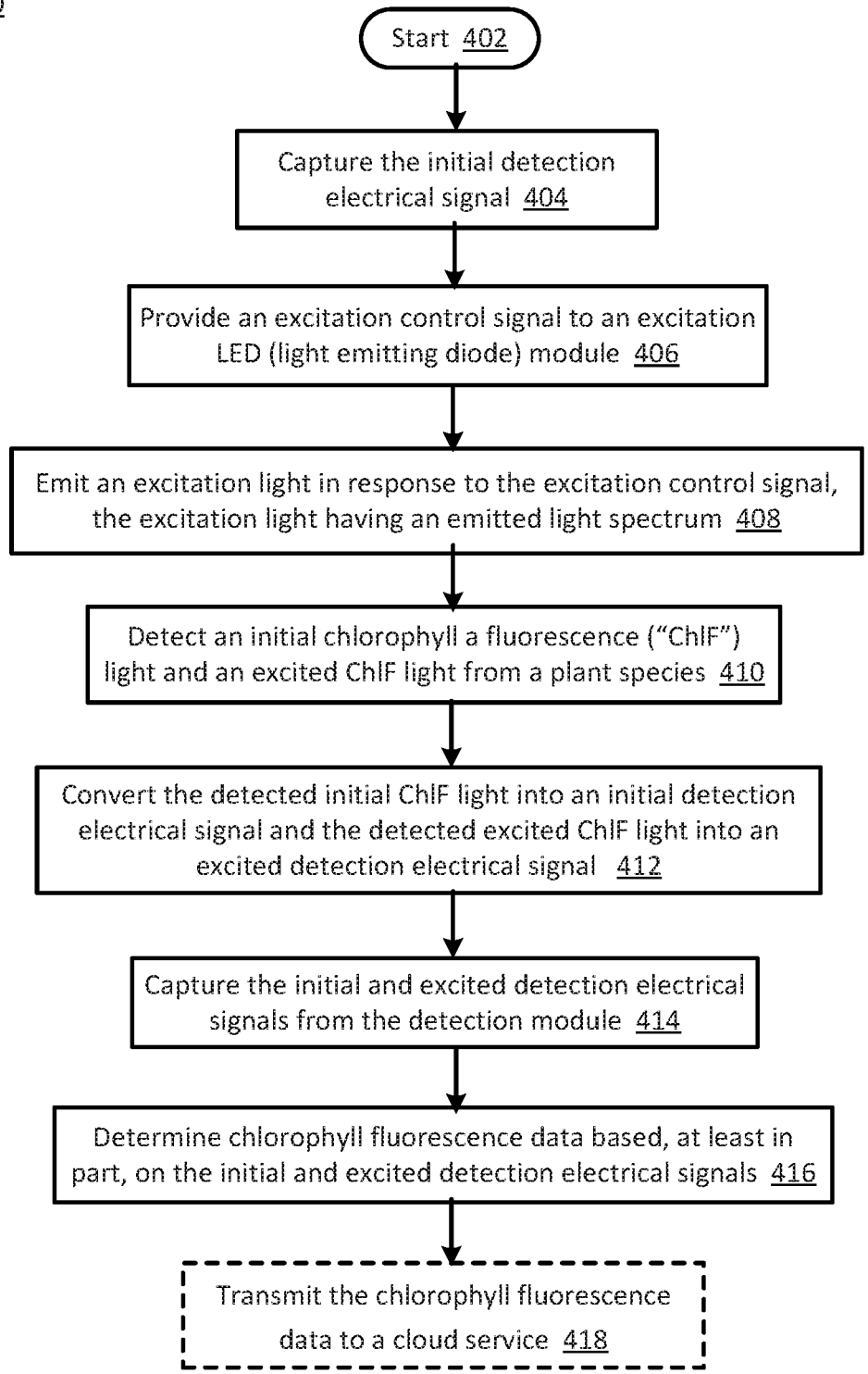
FIG. 4 is a flowchart of example plant fluorometer operations for remote detection of growth dynamics, consistent with several embodiments of the present disclosure.

FIG. 4 is a flowchart of example plant fluorometer operations for remote detection of growth dynamics consistent with several embodiments of the present disclosure. In particular, the flowchart 400 illustrates detecting initial chlorophyll a fluorescence ("ChlF") light and an excited ChlF light from a plant species and determining chlorophyll fluorescence data based, at least in part, on the initial and excited detection electrical signals. The operations of flowchart 400 may be performed by, for example, sensing circuitry 102 (e.g., excitation LED module 110, detection module 130 and controller module 150-1) of FIG. 1.

Operations of flowchart 400 may begin with start at operation 402. The initial detection electrical signal may be captured at operation 404. An excitation control signal may be provided to an excitation LED (light emitting diode) module at operation 406. Operation 408 includes emitting an excitation light in response to the excitation control signal. The excitation light has an emitted light spectrum. Operation 410 includes detecting an initial chlorophyll a fluorescence ("ChlF") light and an excited ChlF light from a plant species. The detected initial ChlF light may be converted into an initial detection electrical signal and the detected excited ChlF light may be converted into an excited detection electrical signal at operation 412. Operation 414 includes capturing the initial and excited detection electrical signals from the detection module. The chlorophyll fluorescence data may be determined based, at least in part, on the initial and excited detection electrical signals at operation 416. In some embodiments, the chlorophyll fluorescence data may be transmitted to a cloud service at operation 418.

As used in any embodiment herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may include, for example, singly or in any combination, hard-wired circuitry, programmable circuitry such as computer processors including one or more individual instruction processing cores, state machine circuitry, and/or firmware that stores instructions executed by programmable circuitry. The logic and/or module may, collectively or individually, be embodied as circuitry that forms part of a larger system, for example, an integrated circuit (IC), an application-specific integrated circuit (ASIC), a field-programmable gate array (FPGA), a programmable logic device (PLD), a complex programmable logic device (CPLD), a system on-chip (SoC), etc.

Memory circuitry 154, 174 may each include one or more of the following types of memory: semiconductor firmware memory, programmable memory, non-volatile memory, read only memory, electrically programmable memory, random access memory, flash memory, magnetic disk memory, and/or optical disk memory. Either additionally or alternatively system memory may include other and/or later-developed types of computer-readable memory.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

EXAMPLES

Without wishing to be bound by theory, the increases in measured fluorescence may be due to growth and not changes in leaf pigmentation, especially chlorophyll a, as will be discussed in greater detail below. It is contemplated that the light provided by the light sources may be adjusted in response to growth rate measurements reported by the photodiode module, e.g., to optimize growth dynamics. In some embodiments, the collected fluorescence data may be sent to a remote location for storage, analysis, or combinations thereof, e.g., cloud service 106, with analysis by cloud analysis application 178. In some embodiments, the systems of the present disclosure may be in communication with a control module to provide data used for controlling a CEA lighting system.

The examples below are related to quantifying the relationship between growth and measured ChlF and to demonstrate that ChlF data remotely collected as described herein may serve as an accurate proxy for plant growth and/or may represent a growth characteristic.

In one example, growth kinetic analyses on a red lettuce cultivar Rouxai were performed using a standard method of time series biomass collection and a model created from an apparatus, system and method consistent with the present disclosure. In this example, lighting was sole source, i.e., no sun.

Above ground fresh (FW) and dry (DW) weights and plant area (PA) were measured at intervals over a 17 day growth period. Three plants were sampled from random positions in the growth tray at 12 time points (5, 7, 9, 10, 11, 12, 13, 14, 15, 16, and 17 days after seeding (DAS)). Fresh weights (g) of individual plants were measured immediately after harvest and digitally photographed on a well-lighted, flat surface next to a 2 cm² red scaling square to measure plant area (PA). The area of green pixels in each photograph was calculated. Individual plants were dried to constant weight in a drying oven at 70 C. Plants were cooled prior to each weighing in a desiccator with calcium sulfate ($CaSO_4$) desiccant until they reached a constant weight (approx. 72 h). Harvests were performed at the same time (2 h into the photoperiod) each day and were synchronized so that plants were always harvested immediately after a ChlF measurement. An additional three plants were sampled at five of the 12 time points described above (9, 11, 13, 15, and 17 DAS) to measure chlorophyll, carotenoid, and anthocyanin concentrations.

Plants were flash frozen in liquid nitrogen ($N_2$) and ground to a fine powder immediately after removal from the growth chamber. Two samples of 20 and 50 mg of ground plant tissue were collected from each plant for anthocyanin and chlorophyll/carotenoid extraction, respectively. Samples were stored in liquid $N_2$ until use. All samples were measured spectrophotometrically using a same spectrophotometer.

In this example, the excitation LED module included four separate, three chip royal blue (447 nm) LED units for a total of 12 LEDs per excitation module. The photon flux density at crop level for the excitation pulses was 2000 µmol m$^{-2}$s$^{-1}$ PAR. The LEDs were driven by an LED driver module with power conditioning configured to prevent LED overload. The frequency was adjustable and, for these examples, the LED driver module was set to receive a 200 Hz excitation signal from a microcontroller via a 200 Hz coaxial signal cable.

The detection module included two photodiodes configured to detect light of wavelengths of 680 nm and 740 nm, respectively. Each photodiode was equipped with a near collimated optical filter configured to limit incoming light to the target wavelengths and field of view. This resulted in a field of view of 12 cm diameter at a distance of 50 cm from the plant canopy. Larger fields of view were possible at a greater distance from the canopy, but were limited based on the dimensions of the growth chamber. The detection module was housed in a custom-built aluminum box milled from 6061 aluminum with wall thicknesses of ¼ inch that shielded the detection electronics from ambient electrical interference.

In this example, the system utilized a separate printed circuit board PCBP to process signals from each photodiode. The boards were powered by a 12 V power supply, with a 5 V output to the photodiodes and microcontroller. The board included a microcontroller (an example of processing unit 152 of FIG. 1) that controlled the excitation LED module (an example of excitation LED module 110). Excitation control signals from the microcontroller to the excitation LED module were carried by a coaxial cable attached to the board via an SMA (SubMiniature version A) connector. Excitation control signals (including excitation pulse, as described herein) to the LED module were controlled by a controller application (an example of controller application 166), executing on the microcontroller. Light at the desired wavelengths was absorbed by the photodiode (an example of photodetector 136-1) and converted to an analog detection electrical signal that was passed to a pre-processing amplification circuitry then through a lock-in amplifier configured to remove a signal with a frequency other than 200 Hz. A low-pass filter and amplifier then removed harmonic signals.

The resulting data was stored in a database (e.g., data store 182) located in the cloud via a wireless network connection.

The power supplies for the excitation LED module and the microcontroller printed circuit boards (PCBs) accepted standard 120 V, 60 Hz AC power as input and provided as output 12 V power to the PCB boards and LED module. The LED driver board was connected to the microcontroller PCB via a BNC cable.

Rouxai red lettuce seeds were obtained and seeded in plugs in standard 1020 flats with 6 13 inserts at a constant day/night temperature of 23° C. and relative humidity of 70%. Plants were grown under 24 h photoperiods for 17 days at 200 µmol m$^{-2}$s$^{-1}$ PAR under cool white fluorescent (CWF) tubes and watered with half strength Hoagland's solution.

ChlF was monitored (using, for example, sensing circuitry 102) at 15 min intervals over a 17 day growth period. To measure ChlF at each time point, groups of five measurements were taken both before and during the 0.8 s excitation pulse (FIG. 3). The lowest and highest of the five measurements were dropped, and the remaining three measurements were averaged to arrive at the final value. ChlF was then calculated as the difference between averaged measurements before each pulse (i.e., an initial chlorophyll a fluorescence ("ChlF") light corresponding to an initial detection electrical signal) and those during each pulse (i.e., an excited ChlF light corresponding to an excited detection electrical signal). A black cloth control experiment demonstrated that ChlF signals emanating from plants were an order of magnitude larger than background noise. Models were constructed for each of FW, DW, and PA plotted as a function of ChlF$_{740\ nm}$ using polynomial regression as implemented by the 'train' function in the R package 'caret'. Leave-one-out cross-validation (LOOCV) was used as a resampling based performance measure for model validation and selection. Prediction intervals were estimated using the 'predict' function in the R package 'stats'. The forward-stepwise selection procedure was used to select the order of each polynomial model (i.e., a stepwise increase in the model order until the t-test for the highest order term is non-significant). Normalized root mean square error (NRMSE) was calculated as a basis for comparison of error between models using the following formula:

$$NRMSE = \frac{RMSE}{ymax - ymin} \quad (1)$$

where RMSE is the root mean square error for the regression model and ymax and ymin are the maximum and minimum values, respectively, of the dependent variable. Polynomial models constructed based on data from each of the two data processing strategies described above were used to predict DW and PA. Predicted values of DW and PA from each model were used to calculate the relative growth rate (RGR), leaf area ratio (LAR), and net assimilation rate (NAR) using the following equations:

$$RGR = \frac{\ln W_2 - \ln W_1}{t_2 - t_1} \quad (2)$$

$$LAR = \frac{1}{2}\left(\frac{A_1}{W_1} + \frac{A_2}{W_2}\right) \quad (3)$$

$$NAR = \left(\frac{W_2 - W_1}{t_2 - t_1}\right)\left(\frac{\ln A_2 - \ln A_1}{A_2 - A_1}\right) \quad (4)$$

where $W_1$ and $W_2$ are the dry weight for the first and second time point, respectively, $A_1$ and $A_2$ are the plant area for the first and second time point, respectively, and $t_1$ and $t_2$ are the days after seeding for the first and second time points, respectively. Time points used in index calculations were chosen from the linear portion of plots of time versus natural log-transformed DW to ensure that they were within the exponential region of the growth curve. To avoid transformation bias, DW data for all replicates and time points were natural log transformed before calculating means and standard errors. Indices were calculated using observed and predicted values from identical time points for each experimental replicate (n=4), and results were averaged to obtain final mean and standard error. RGR, LAR, and NAR calculated from predicted DW and PA were then compared to RGR, LAR, and NAR calculated from observed values to determine the accuracy of predicted values.

Pearson correlation coefficients and p-values were calculated for all combinations of measured variables (i.e., FW, DW, PA and ChlF; see Table 1) using the 'rcorr' function implemented in the R package Hmisc V4,1-0. Significance testing of differences between pigment levels at different time points was carried out using Student's t-test.

Relative importance analysis of FW, DW, and PA as predictors of ChlF was carried out using the LMG measure as implemented by the 'calc.relimp' function in the R package 'relaimpo'. This method was selected for its ability to account for a high degree of multicollinearity between predictor variables.

It may be appreciated that methods and systems of the present disclosure appear to have a relatively simpler construction compared to current amplitude modulated fluorometer technology and protocols, and provide real-time tracking of physical plant growth parameters in a controlled environment. The systems of the present disclosure can also work remotely while being separable, increasing functionality, efficiency, and ease-of-use.

Systems and methods of the present disclosure demonstrate that far red ChlF emission at 740 nm (ChlF$_{740\ nm}$) measured in the light-adapted state is correlated with observed changes in FW, DW and PA of experimental plants (see Table 1). It may thus serve as a simple, remotely-measured proxy for plant growth without computationally expensive data processing or standard destructive methods. Adding biological inputs to CEA control algorithms can improve crop management and resource use efficiency.

Manually- and remotely-sensed growth kinetics for red lettuce were performed and compared, ChlF measured both at 680 nm and 740 nm were collected and followed similar trends. ChlF$_{740\ nm}$ was used for the following analyses as it was a relatively more robust and stable signal during the experimental periods.

Pearson correlation coefficients (r) and p-values were calculated to determine the strength and direction of the relationship between all combinations of measured variables (see Table 1). ChlF showed a relatively strong positive correlation with all measured quantities.

TABLE 1

Pearson correlation coefficients and p-values for correlations between measured quantities.

| | Pearson Correlation Coefficient (r) | | | | Pearson Correlation Coefficient p-Value | | | |
|---|---|---|---|---|---|---|---|---|
| | ChlF | FW | DW | PA | ChlF | FW | DW | PA |
| ChlF | 1 | 0.921 | 0.934 | 0.947 | NA | $5.697 \times 10^{-5}$ | $2.677 \times 10^{-5}$ | $1.024 \times 10^{-5}$ |
| FW | 0.921 | 1 | 0.995 | 0.996 | $5.697 \times 10^{-5}$ | NA | $1.943 \times 10^{-10}$ | $6.773 \times 10^{-11}$ |
| DW | 0.934 | 0.995 | 1 | 0.998 | $2.677 \times 10^{-5}$ | $1.943 \times 10^{-10}$ | NA | $5.366 \times 10^{-12}$ |
| PA | 0.947 | 0.996 | 0.998 | 1 | $1.024 \times 10^{-5}$ | $6.773 \times 10^{-11}$ | $5.366 \times 10^{-12}$ | NA |

NA = Not applicable, ChlF = Chlorophyll fluorescence at 740 nm, FW = Fresh weight, DW = Dry weight, PA = Plant area.

Chlorophyll and carotenoid concentrations were assayed at five time points between nine days after seeding (DAS) and 17 DAS. No significant change in mean chlorophyll a (Chla) or carotenoid content was observed in harvested plants during this period. Conversely, mean chlorophyll b (Chlb) concentrations significantly increased from 9 DAS to 13 DAS (p<0.05), after which no significant change was observed. Anthocyanin concentrations were measured at the same time intervals as chlorophylls and carotenoids and increased 1.6-fold from 9 DAS to 15 DAS (p<0.001) after which they remained stable.

The relationship between mean ChlF and mean fresh weight (FW), dry weight (DW), and plant area (PA) was quantified using polynomial regression. The root mean square error (RMSE) of all final models normalized to the observed range of values for the modeled variable was less than 5%, with the models for PA and DW as a function of ChlF having the lowest (3.2%) and highest (4.1%) NRMSE, respectively. The trend was the same for the average NRMSE for models built from LOOCV training sets, which was highest for DW (6.2%) and lowest for PA (3.7%).

Multiple linear regression modeling of $ChlF_{740\ nm}$ as a function of FW, DW and PA was followed by relative importance analysis to investigate sources of variation in mean ChlF. Plant area (PA) explained 4.7% and 5.3% more of the variance in CUE than FW and DW, respectively.

Commonly-used growth indices were calculated from mean observed and predicted values of FW, DW and PA to evaluate model performance and demonstrate that measured ChlF could serve as an adequate proxy for these physical growth parameters. No significant differences were observed between the average values of growth indices calculated from observed values.

It is contemplated that the positive correlation observed between $ChlF_{740\ nm}$ and PA, FW, and DW has two possible explanations. First, because fluorescence at 740 nm is emitted by chlorophyll a (Chla) molecules, the observed increase in $ChlF_{740\ nm}$ could potentially be the result of increasing concentrations of Chla relative to total plant mass. However, Chla concentrations in the experimental plants did not change significantly over the course of the experiment, indicating that Chla concentrations were not responsible for the observed increases in $ChlF_{740\ nm}$. Red lettuce also contains the red pigment anthocyanin that acts as a sunscreen and functions to attenuate light from reaching the photosynthetic apparatus where Chla molecules are located. This attenuating effect could also reduce the level of light from $ChlF_{740\ nm}$ being emitted from the leaf. However, while anthocyanin concentrations did increase during growth, the correlation between the $ChlF_{740\ nm}$ signal and PA, FW, and DW indicates that the presence of anthocyanin did not attenuate the ChlF signal significantly during growth. Together with the lack of any variation in Chla content over the course of the experiment, it is contemplated that physiological changes, rather than biochemical changes, in the plant may be driving the observed changes in $ChlF_{740\ nm}$. Second, given that Chla resides in the chloroplasts within plant cells, it is possible that the majority of the variation in ChlF740 nm can be explained by changes in the overall photosynthetic surface area exposed to the excitation pulse emitted by the detector. Consistent with this suggestion, relative weights analysis of a multiple linear regression model of $ChlF_{740\ nm}$ as a function of FW, DW, and PA indicated that PA explained roughly 5% more of the total explained variance in $ChlF_{740\ nm}$ than FW or DW. It is contemplated that this result may explain why $ChlF_{740\ nm}$ plotted as a function of time approached an upper asymptote in three of four experimental replicates. Once PA became large enough to fill the area of effect of the excitation light and photodiode module, the photosynthetic surface area (and, as a result, ChlF) would no longer increase. Due to space constraints in the growth chambers, the plants were grown until the baby leafy green stage (17 days). The growth curves indicated that the lettuce crop was still in exponential growth and had not reached the stationary phase when full heads would be harvested. Initial testing in a greenhouse did reveal that the optical system was operational in full sun without saturation issues.

Plotting FW, DW, and PA as a function of $ChlF_{740\ nm}$ revealed a nonlinear relationship between plant growth and fluorescence emission that was best described by polynomial regression modeling. Normalized root mean square error (NRMSE) of models varied from 3.3% to 4.1% of the predicted variable's range, indicating both a relatively small difference between predicted and observed values for each model, and a consistent predictive accuracy across models. These NRMSE values also compare favorably to those of previous models of plant growth as a function of ChlF. For example, linear models based on the natural log (ln) of basil plant dry weight as a function of the ln of the ratio of red to far red ChlF resulted in NRMSE values of between 5.1% and 7.4%, as compared to an NRMSE of 4.1% for the polynomial models of dry weight as a function of $ChlF_{740\ nm}$ in this study. In addition, ln-transformation of DW introduces an additional layer of complexity to the interpretation of model predictions, and may result in statistically-biased predictions. The measurements of a single ChlF wavelength and polynomial modeling from untransformed data both avoids these potential statistical pitfalls and may make the prediction of growth parameters from ChlF data more practical for the grower.

Values for RGR, NAR, and LAR calculated from predicted mean values for DW and PA were within 10% of those calculated from observed mean values of DW and PA, though the difference was not statistically significant. Examples of studies utilizing RGR, NAR, and LAR from the literature indicate that 10% variation is well within the typical error range for these indices. These results demonstrate that ChlF$_{740\ nm}$ measured by the systems according to some embodiments of the present disclosure can serve as a proxy for plant growth that has potential applications in physiological and ecophysiological research, as well as commercial CEA settings. One such application is made possible by recent advances in light emitting diode (LED) systems which have provided a relatively level of lighting control through feedback and dynamic algorithms. Such control may offer growers the opportunity to maximize light use efficiency and optimize morphological and physiological characteristics of their crop through manipulation of spectral composition. It is contemplated that the ability of the systems of the present disclosure to report real-time physiological data may make it a candidate for integration into such light control systems, without expensive equipment, computationally expensive calculations, or labor-intensive data collection.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. An apparatus for remote detection of plant growth dynamics, the apparatus comprising:
   an excitation LED (light emitting diode) module comprising at least one LED, each LED configured to emit an excitation light in response to an excitation control signal, the excitation light having an emitted light spectrum;
   a detection module comprising a photodetector configured to detect an initial chlorophyll a fluorescence ("ChlF") light and an excited ChlF light from a plant species, the photodetector further configured to convert the detected initial ChlF light into an initial detection electrical signal and the detected excited ChlF light into an excited detection electrical signal, the excited ChlF light emitted from the plant species in response to receiving the excitation light; and
   a controller module coupled to the excitation LED module and the detection module, the controller module configured to provide the excitation control signal to the excitation module, to capture the initial and excited detection electrical signals from the detection module and to determine chlorophyll fluorescence data based, at least in part, on the initial and excited detection electrical signals, the excitation control signal comprising an excitation pulse, the excitation pulse comprising a pulse train defined by a plurality of excitation pulse parameters comprising a maximum current amplitude, a duty cycle, an excitation pulse period ($T_E$), a pulse train pulse period ($T_P$) and an excitation pulse fundamental frequency, a respective value of each of the plurality of the excitation pulse parameters related to a growth dynamic of the plant species and the controller module is configured to capture the initial detection electrical signal prior to capturing the excited detection electrical signal;
   wherein the excitation LED module and the detection module are configured to be positioned remotely from the plant species, and wherein the chlorophyll fluorescence data represents a growth characteristic of the plant species.

2. The apparatus according to claim 1, wherein the controller module is further configured to transmit the chlorophyll fluorescence data to a cloud service.

3. The apparatus according to claim 1, wherein the excitation light has a wavelength of about 447 nanometers (nm) and each ChlF light has a wavelength selected from the group comprising about 680 nm and about 740 nm.

4. The apparatus according to claim 1, wherein the growth characteristic is selected from the group comprising relative growth rates (RGR), net assimilation rates (NAR), plant area (PA), leaf area ratio (LAR), or combinations thereof.

5. The apparatus according to claim 4, wherein a relationship between a selected growth characteristic and the chlorophyll fluorescence data corresponds to a polynomial regression.

6. The apparatus according to claim 1, wherein the photodetector is selected from the group comprising a photodiode and a phototransistor, the detection module further comprises a collimator coupled to the photodetector, and the controller module comprises a processing unit, a preprocessing amplifier, a lock in amplifier and a gain and filter stage, the processing unit selected from the group comprising a single core processing unit, a microcontroller, an application-specific integrated circuit (ASIC), a field programmable gate array (FPGA) and a programmable logic device (PLD), the lock in amplifier configured to pass a portion of each of the detection electrical signals, the portion having a fundamental frequency corresponding to a fundamental frequency of the excitation control signal.

7. The apparatus according to claim 1 wherein the maximum current amplitude corresponds to a photon flux density at a canopy of the plant species of 2000 micromoles of light per square meter per second ($\mu$mol m$^{-2}$s$^{-1}$) photosynthetically-active radiation (PAR), the duty cycle is 50 percent, the excitation pulse period ($T_E$) is in the range of 0.5 seconds to 1 second, and the excitation pulse fundamental frequency is 200 hertz (Hz) corresponding to the pulse train pulse period ($T_P$) of 5 milliseconds.

8. A method for remote detection of plant growth dynamics, the method comprising:
   providing, by a controller module, an excitation control signal to an excitation LED (light emitting diode) module;
   emitting, by at least one LED included in the excitation LED module, an excitation light in response to the excitation control signal, the excitation light having an emitted light spectrum;
   detecting, by a photodetector included in a detection module, an initial chlorophyll a fluorescence ("ChlF") light and an excited ChlF light from a plant species;
   converting, by the photodetector, the detected initial ChlF light into an initial detection electrical signal and the detected excited ChlF light into an excited detection electrical signal, the excited ChlF light emitted from the plant species in response to receiving the excitation light;
   capturing, by the controller module, the initial and excited detection electrical signals from the detection module, the initial detection electrical signal captured prior to capturing the excited detection electrical signal, the excitation control signal comprising an excitation pulse, the excitation pulse comprising a pulse train defined by a plurality of excitation pulse parameters comprising a maximum current amplitude, a duty cycle, an excitation pulse period ($T_E$), a pulse train pulse period ($T_P$) and an excitation pulse fundamental frequency, a respective value of each of the plurality of the excitation pulse parameters related to a growth dynamic of the plant species; and determining, by the controller module, chlorophyll fluorescence data based, at least in part, on the initial and excited detection electrical signals;

wherein the excitation LED module and the detection module are configured to be positioned remotely from the plant species, and wherein the chlorophyll fluorescence data represents a growth characteristic of the plant species.

9. The method according to claim 8, further comprising transmitting, by the controller module, the chlorophyll fluorescence data to a cloud service.

10. The method according to claim 8, wherein the excitation light has a wavelength of about 447 nanometers (nm) and each ChlF light has a wavelength selected from the group comprising about 680 nm and about 740 nm.

11. The method according to claim 8, wherein the growth characteristic is selected from the group comprising relative growth rates (RGR), net assimilation rates (NAR), plant area (PA), leaf area ratio (LAR), or combinations thereof.

12. The method according to claim 11, wherein a relationship between a selected growth characteristic and the chlorophyll fluorescence data corresponds to a polynomial regression.

13. The method according to claim 8, wherein the photodetector is selected from the group comprising a photodiode and a phototransistor, the detection module further comprises a collimator coupled to the photodetector, and the controller module comprises a processing unit, a preprocessing amplifier, a lock in amplifier and a gain and filter stage, the processing unit selected from the group comprising a single core processing unit, a microcontroller, an application-specific integrated circuit (ASIC), a field programmable gate array (FPGA) and a programmable logic device (PLD), the lock in amplifier configured to pass a portion of each of the detection electrical signals, the portion having a fundamental frequency corresponding to a fundamental frequency of the excitation control signal.

14. The method according to claim 8, wherein the maximum current amplitude corresponds to a photon flux density at a canopy of the plant species of 2000 micromoles of light per square meter per second ($\mu mol\ m^{-2}s^{-1}$) photosynthetically-active radiation (PAR), the duty cycle is 50 percent, the excitation pulse period ($T_E$) is in the range of 0.5 seconds to 1 second, and the excitation pulse fundamental frequency is 200 hertz (Hz) corresponding to the pulse train pulse period ($T_P$) of 5 milliseconds.

15. A system for remote detection of plant growth dynamics, the system comprising:

sensing circuitry comprising:
an excitation LED (light emitting diode) module comprising at least one LED, each LED configured to emit an excitation light in response to an excitation control signal, the excitation light having an emitted light spectrum;

a detection module comprising a photodetector configured to detect an initial chlorophyll a fluorescence ("ChlF") light and an excited ChlF light from a plant species, the photodetector further configured to convert the detected initial ChlF light into an initial detection electrical signal and the detected excited ChlF light into an excited detection electrical signal, the excited ChlF light emitted from the plant species in response to receiving the excitation light; and a controller module coupled to the excitation LED module and the detection module, the controller module configured to provide the excitation control signal to the excitation module, to capture the initial and excited detection electrical signals from the detection module and to determine chlorophyll fluorescence data based, at least in part, on the initial and excited detection electrical signals, the excitation control signal comprising an excitation pulse, the excitation pulse comprising a pulse train defined by a plurality of excitation pulse parameters comprising a maximum current amplitude, a duty cycle, an excitation pulse period ($T_E$), a pulse train pulse period ($T_P$) and an excitation pulse fundamental frequency, a respective value of each of the plurality of the excitation pulse parameters related to a growth dynamic of the plant species and the controller module is configured to capture the initial detection electrical signal prior to capturing the excited detection electrical signal;

wherein the excitation LED module and the detection module are configured to be positioned remotely from the plant species, and wherein the chlorophyll fluorescence data represents a growth characteristic of the plant species; and a cloud service coupled to the sensing circuitry via a network, the cloud service comprising a data store, the controller module configured to transmit the chlorophyll fluorescence data to the cloud service for storage in the data store.

16. The system of claim 15, wherein the growth characteristic is selected from the group comprising relative growth rates (RGR), net assimilation rates (NAR), plant area (PA), leaf area ratio (LAR), or combinations thereof.

17. The system of claim 16, wherein the cloud service further comprises a cloud analysis application configured to determine a relationship between a selected growth characteristic and the chlorophyll fluorescence data.

18. The system of claim 16, wherein the relationship between the selected growth characteristic and the chlorophyll fluorescence data corresponds to a polynomial regression.

* * * * *